United States Patent
Parekh et al.

(10) Patent No.: US 6,534,321 B1
(45) Date of Patent: Mar. 18, 2003

(54) ASSAYING AND STORING LABELLED ANALYTES

(75) Inventors: Rajesh Bhikhu Parekh, Near Wendlebury (GB); Paul Nicholas Goulding, Cambridgeshire (GB); Dale Robert Pfost, Pennington, NJ (US)

(73) Assignee: Oxford GlycoSciences (UK) Ltd., Abingdon (GB)

( * ) Notice: Subject to any disclaimer, the term of this patent is extended or adjusted under 35 U.S.C. 154(b) by 0 days.

(21) Appl. No.: 09/227,446

(22) Filed: Jan. 8, 1999

Related U.S. Application Data

(63) Continuation of application No. PCT/GB97/01846, filed on Jul. 9, 1997.

(30) Foreign Application Priority Data

Jul. 10, 1996 (GB) .............................. 9614477

(51) Int. Cl.⁷ ............................................ G01N 33/543
(52) U.S. Cl. ................. 436/514; 204/450; 204/456; 204/465; 204/466; 204/600; 422/50; 435/968; 436/516; 436/528
(58) Field of Search ............................. 204/450, 456, 204/465, 466, 469, 600; 422/50; 435/968; 436/514, 516, 528

(56) References Cited

U.S. PATENT DOCUMENTS 5,066,377 A    11/1991  Rosenbaum et al.
5,104,508 A  * 4/1992  Williams et al.
5,205,917 A  * 4/1993  Klock, Jr.
5,308,460 A  * 5/1994  Mazid et al.
5,747,347 A  * 5/1998  Hawke et al.
5,795,720 A    8/1998  Henco et al.
5,898,493 A  * 4/1999  Jankowiak et al. ......... 356/318

FOREIGN PATENT DOCUMENTS

EP    0 251 306 A1    1/1987
WO    WO 91/02815     3/1991
WO    WO 94/28423     12/1994

OTHER PUBLICATIONS

A Laboratory Guide to Glycoconjugate Analysis. BioMethods, vol. 9. Edited by P. Jackson & J.T Gallagher, Apr. 1997.*

* cited by examiner

*Primary Examiner*—Bao-Thuy L. Nguyen
(74) *Attorney, Agent, or Firm*—Pennie & Edmonds LLP

(57) ABSTRACT

A method for analyzing a sample containing a plurality of analytes, comprises labelling the analytes with a detectable label, the label being chosen such that its detectability can be influenced by modifying the conditions of detection; separating the labelled analytes, before or after labeling,; and determining the presence of the separated analytes under the modified conditions and also, if desired, the unmodified conditions. Suitable detection apparatus comprises a support for a gel, means for detecting one or more analytes in the gel, and means for reducing the temperature of the gel to below ambient temperature, e.g., to no more than 0°C.

13 Claims, 1 Drawing Sheet

ASSAYING AND STORING LABELLED ANALYTES

Figure 1:
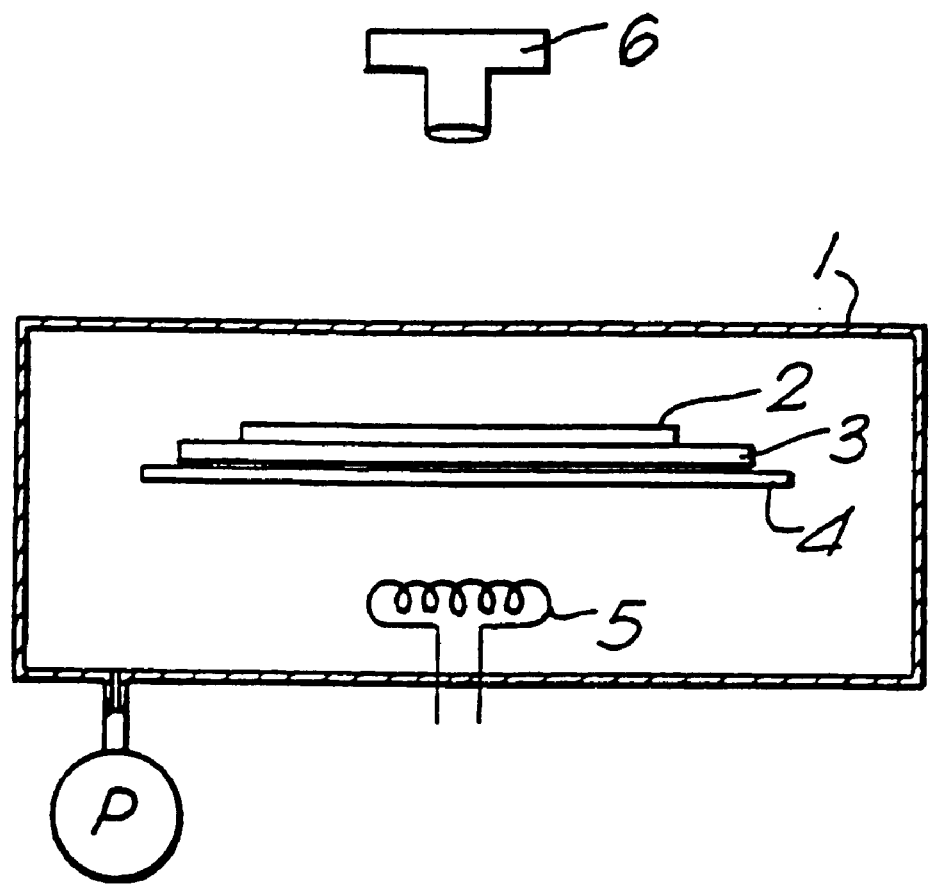

This is a continuation of International Application No. PCT/GB97/01846, filed on Jul. 9, 1997.

FIELD OF THE INVENTION

This invention relates to assays, and especially to gel electrophoresis, to achieve improved imaging and also storage.

BACKGROUND OF THE INVENTION

Separation of mixtures of entities, particularly biomolecules such as proteins and nucleic acids, is commonly performed using electrophoresis in a gel medium, the gel being produced usually from polyacrylamide or agarose. Once separation has been performed, the separated elements are either detected while still in the gel or after transfer to a membrane support, using any of a variety of biochemical, chemical or spectroscopic methods. It is consistently taught by manufacturers of such gels and by the wider prior literature that gels should not be frozen or subjected to temperatures less than 0° C. Otherwise, loss of performance, of the gel's physical integrity, or of sample detection, will result. The current practice of gel electrophoresis therefore consists essentially of the following steps:

(a) gels are prepared or purchased which have not been subjected to a temperature below 0° C.;

(b) such gels are stored at a temperature greater than 0° C. until used;

(c) sample is applied to the gel and then electrophoresis is performed at a temperature greater than 0° C. for the desired period;

(d) the gel is recovered from the electrophoresis apparatus and the location of sample(s) in one or two dimensions of the gel is detected by any one of various standard procedures; and (e) the gel is then fixed, using well-described chemicals or solvents, or alternatively the gel is "blotted" onto one of various membranes using any of the well-described procedures, thereby transferring to the membrane, some or a fraction of each sample without substantial change in the relative spatial distribution between samples. The gel itself is then usually discarded.

SUMMARY OF THE INVENTION

The present invention is based on the realisation that a reduction in temperature can be used to enhance the signal from fluorescent labels used on analytes in gel electrophoresis. This is useful to distinguish between analytes and to enhance distinction from background. This leads to a more general method in which, according to this invention, analytes are labelled with a detectable label, the label being chosen such that its detectability can be influenced by modifying the conditions of detection, the analytes are separated (before or after labelling), and the presence of the separated analytes is determined under the modified conditions. If desired, the presence of the analytes may also be determined under the unmodified conditions, e.g. as a control.

An important aspect of this invention is that gels may be cooled or frozen, apparently without adverse effect. The invention provides some applications of freezing gels to gel storage, e.g. in a sealed pack, and to the detection of samples contained within such gels.

Enhanced detection is particularly evident in use of an electrophoretic gel. Novel apparatus comprises a support for a gel, means for applying a current through the gel, means for detecting analytes in the gel, and also means for maintaining the temperature of the gel at below 10° C., preferably below 5° C., e.g. at 0° C. or below.

DESCRIPTION OF THE INVENTION

The modification to which this invention refers may be of any relevant parameter, as can readily be determined by one of ordinary skill in the art. Modification may be of physical conditions such as temperature, e.g. with respect to ambient conditions. For the purpose of illustration, this invention will be described with reference to modification by cooling.

The invention will be described, by way of example, with reference to detection using an electrophoretic gel. For the purpose of this specification, the term "electrophoretic gel" means a gel matrix, usually polymeric, impregnated with a medium, usually aqueous, in which salts or other conductive species are present; a current can be passed through the gel such that species of interest move through it at rates dependent on their respective characteristics, and those species of different characteristics are separated. Various formats may be used within the scope of this invention, including capillary, one-dimensional tubes, two-dimensional slabs with lanes, two-dimensional gels for two-dimensional separation, and also three-dimensional analysis.

It has been found that gels, e.g. consisting substantially of polyacrylamide, may be reversibly frozen without structural impairment. This is apparently independent of the dimensions of the gel or of its degree of cross-linking or its density. Further, this freezing can be achieved reproducibly and routinely according to a process which is capable of automation.

The freezing of electrophoretic gels allows longer-term storage of gels, without significant deterioration. Moreover, where the gels contain separated samples, freezing has the further benefit of reducing diffusion in the gels, thereby preserving the relative position of individual samples within the gel, thus allowing long-term storage of authentic gels without the need for chemical or solvent fixation or the need to prepare an artificial image. A further advantage of the invention is the dramatic enhancement of the fluorescent signal obtained from fluorescent materials contained within the gel, without significant loss of spatial resolution of the signal. Consequently, sample(s) can be detected with greater sensitivity and resolution in appropriately frozen gels than in unfrozen gels. This effect is apparently unaffected by the nature of the gel or the fluorescent substance.

While an unused electrophoretic gel may be frozen, particular advantages are associated with freezing after the application and electrophoresing of the sample, for storage and/or to enhance the signal from a fluorescent label. The use of fluorescent labels in the analysis of carbohydrates is described in U.S. Pat. No. 5,104,508 and WO-A-9428423. The latter publication discloses the use of 2-aminobenzamide, anthranilic acid and analogous compounds as particularly useful fluorescent markers. Their utility may be increased by means of the present invention.

Labelling may be done before or after separation. For instance, a label may be used which binds non-covalently to analytes after these have already been separated in a gel. The invention may involve modification of a known procedure of this type, such as that in which DNA fragments are separated in a gel, and the gel is then exposed to a label (ethidium bromide) which binds non-covalently to each separated fragment (but not to regions of the gel lacking DNA). The location of individual fragments is then found from the fluorescence of the label.

In a particularly preferred embodiment of the invention, an electrophoretic gel is used, in conventional manner, to separate respective species, to any desired degree, and the gel is then "snap-frozen". This can be an automatic process, in which means for freezing the gel comes into operation at a predetermined time, e.g. when the most mobile species has passed a predetermined distance along the gel. Snap-freezing may be achieved, for example, by sandwiching the gel between two metal plates which have been previously cooled by immersion in, e.g. liquid nitrogen, or dry ice (frozen carbon dioxide), and will usually involve cooling the gel from ambient temperature to a temperature below 0° C., e.g. −10° C. or down to −40° C., over a period of less than 1 minute, preferably less than 30 seconds, in order to achieve the desired phase transition. The frozen gel, including separated species, can then be stored until required for analysis. Immediate analysis may benefit from the improved signal, as described above. When storage is the intention, the electrophoresis apparatus may not itself require detection means. If desired, the apparatus may include means for evacuating water and/or for introducing an inert atmosphere such as argon.

Separation of the analytes and modification of the signal may be simultaneous. In another embodiment of the invention, electrophoresis or other separation technique may be conducted in conventional manner, followed by collection of the separated sample and modification of the sample, e.g. by cooling. For example, gels may be produced and collected continuously, and passed on to a substrate, e.g. a supporting tape, which can itself be cooled or which is passed to a cooling and detection station.

Cooling gives an enhanced fluorescent signal. This or other means of modifying a suitable signal may give, for example, a shift in the wavelength of emitted photons. Any such modification can be associated with appropriate detection means, known or modified as necessary. If the method is conducted on a continuous basis, it may be desirable to read results continuously or at intervals. A time-gated system may be appropriate.

Apparatus for use in this invention may comprise gel electrophoresis apparatus with cooling means, or gel electrophoresis apparatus coupled with a cooled storage device. The accompanying drawing illustrates such apparatus schematically.

The embodiment shown in FIG. 1 comprises a chamber 1 to which a vacuum pump P is connected. The pump is used to provide a low degree of vacuum in the chamber 1, thereby decreasing frosting/humidity.

Within the chamber 1 are provided a gel 2 to be analysed, resting on a clear plate 3, e.g. of quartz. This combination is cooled by a cooling plate 4. The plate 4 may be removable, and introduced after cooling externally in, say, dry ice. Alternatively, the plate 4 may be cooled in situ, e.g. by the provision of circulating cooling liquid such as liquid $N_2$. A UV source 5 is provided, to excite labelled species in the gel 2. There is also an imaging device 6.

Apparatus such as that shown may be used to analyse a gel in which analytes have previously been separated. It may also comprise means for separation in situ, e.g. means for applying a current to the gel, of conventional type.

The present invention has many applications, i.e. beyond the given advantages associated with storage, shipping or prolonged utility of gels. Freezing of gels can have valuable applications in clinical diagnostics and forensic medicine, the separation and/or detection of proteins, nucleic acids or carbohydrates, DNA sequencing, and applications of amplification such as PCR.

The following Example illustrates the invention.

EXAMPLE

Oligosaccharides were labelled and separated by PAGE. In each test, an oligosaccharide sample (containing 10 nanomoles) was labelled by dissolving it in a solution of 30% (v/v) acetic acid in DMSO (dimethyl sulphoxide) containing 0.35 M anthranilic acid. The solution was heated at 65° C. for 2 hours, and then an aliquot of each sample was loaded onto a lane of the gel.

PAGE analysis of anthranilic acid-labelled glycans was then conducted. Gels of thickness 0.75 mm were prepared as follows: a stacking gel (T=C=5%) 4 mm long was provided in a gel buffer of 0.125 M Tris.HCl , pH 6.8, above a resolving gel (T=22%, C=5%) of length 55 mm in a buffer of 0.375 M Tris.HCl, pH 8.8. The running buffer was 40 mM Tris.borate, pH 8.5, and gels were run at a constant current of 15 mA for 75 minutes. Sample was loaded in 4 μl of a sample buffer of composition 0.125 M Tris.HCl, pH 6.8, containing 5% (v/v) glycerol. Gels were viewed and photographed over a UV trans-illuminator with a maximum $\lambda_{emiss}$ of 312 nm.

Photographs were taken of each gel after it was run in conventional manner, as a control, and after it was snap-frozen. Samples were run in the lanes as follows:

Lane 1: 50 μg of dextran oligomers

Lane 2: 25 μg of dextran oligomers

Lane 3: 20 μg of oligomers from bovine serum fetuin

Lane 4: 20 μg of oligomers from bovine pancreatic ribonuclease B

Lane 5: 20 μg of oligomers from hen egg ovalbumin

Lane 6: 20 μg of oligomers from human α-acid glycoprotein

Lane 7: as for Lane 2

Lane 8: as for Lane 1

In the control, visualisation with a 120-second exposure gave distinct bands. When the same gel was visualised after snap-freezing, with a 30-second exposure, an approx. 10–20× increase in signal intensity was observed.

What is claimed is:

1. A method of detecting one or more labeled analytes in an electrophoretic slab gel containing a plurality of electrophoretically separated analytes, comprising the steps of:

(a) after the electrophoretic separation, subjecting the gel to a temperature below 0° C.; and (b) following step (a), detecting-one or more labeled analytes in the gel while maintaining the gel at a temperature below +10° C.

2. The method of claim 1, wherein step (a) comprises snap freezing the gel.

3. The method of claim 2, further comprising storing the frozen gel prior to performing step (b).

4. The method of claim 1, wherein step (a) comprises subjecting the gel to a temperature between 0° C. and −40° C.

5. The method of claim 1, 2, or 3, wherein the temperature of step (b) is below +5° C.

6. The method of claim 5, wherein the temperature of step (b) is 0° C. or below.

7. The method of claim 1, wherein the one or more labeled analytes have been labeled with a fluorescent marker prior to or following the electrophoretic separation.

8. The method of claim 1, wherein the slab gel comprises a plurality of lanes.

9. The method of claim 1, wherein the analytes have been separated by two-dimensional electrophoresis.

10. The method according to claim 1, wherein the analytes are biomolecules.

11. The method according to claim 1, wherein the analytes are proteins.

12. The method according to claim 1, wherein the analytes are nucleic acids.

13. The method according to claim 1, wherein the analytes are carbohydrates.

* * * * *